United States Patent [19]
Doerfel

[11] Patent Number: 5,531,228
[45] Date of Patent: *Jul. 2, 1996

[54] DETECTOR SYSTEM FOR DIRECT INTERNAL DOSIMETRY IN HUMAN BEINGS

[75] Inventor: Hans Doerfel, Karlsruhe, Germany

[73] Assignee: Kernforschungszentrum Karlsruhe GmbH, Karlsruhe, Germany

Related U.S. Application Data

[63] Continuation-in-part of PCT/EP93/01783, Jul. 8, 1993.

[21] Appl. No.: 354,203

[22] Filed: Dec. 12, 1994

[30] Foreign Application Priority Data

Jul. 10, 1992 [DE] Germany ............ 42 22 661.9

[51] Int. Cl.⁶ ............................................. A61B 6/00
[52] U.S. Cl. .................. 128/653.1; 128/654; 128/659; 250/363.02; 250/363.08
[58] Field of Search ................. 128/653.1, 654, 128/659; 250/336.1, 361 R, 367, 362, 363.02, 363.08, 370.11

[56] References Cited

U.S. PATENT DOCUMENTS

| | | | |
|---|---|---|---|
| 4,352,019 | 9/1982 | Pollard. | |
| 4,632,123 | 12/1986 | Govaert et al. | 128/659 |
| 4,712,561 | 12/1987 | Wagner, Jr. | 128/659 |

FOREIGN PATENT DOCUMENTS

0196359 10/1986 European Pat. Off. .

OTHER PUBLICATIONS

Kerntechnik, vol. 19 No. 11 Nov. 1977, Munich Germany p. 507, Cainberra elektronik GmbH.
Health Physics, vol. 16, No. 6, Jun. 1969 Ireland pp. 719–729 CHABRA AS p. 720.
IEEE Trans. on Nuclear Science, vol.–NS–34, No. 1, 1987 pp. 606–610.

*Primary Examiner*—Krista M. Zele
*Attorney, Agent, or Firm*—Klaus J. Bach

[57] ABSTRACT

In a detector system for direct internal dosimetry of persons which comprises at least three gamma radiation detectors mounted on a support structure including a seat-like structure on which a person is supported in a seated position, the support structure has a first one of the detectors mounted thereon such that its central axis is directed toward the lungs of the person, a second detector mounted into the seat-like structure such that its central axis is directed upwardly toward the center of the digestive tract and a third detector arranged so that it is disposed above and its unshielded face is directed downwardly toward the legs of the person being checked for determining gamma ray emission from the whole body of said person.

5 Claims, 1 Drawing Sheet

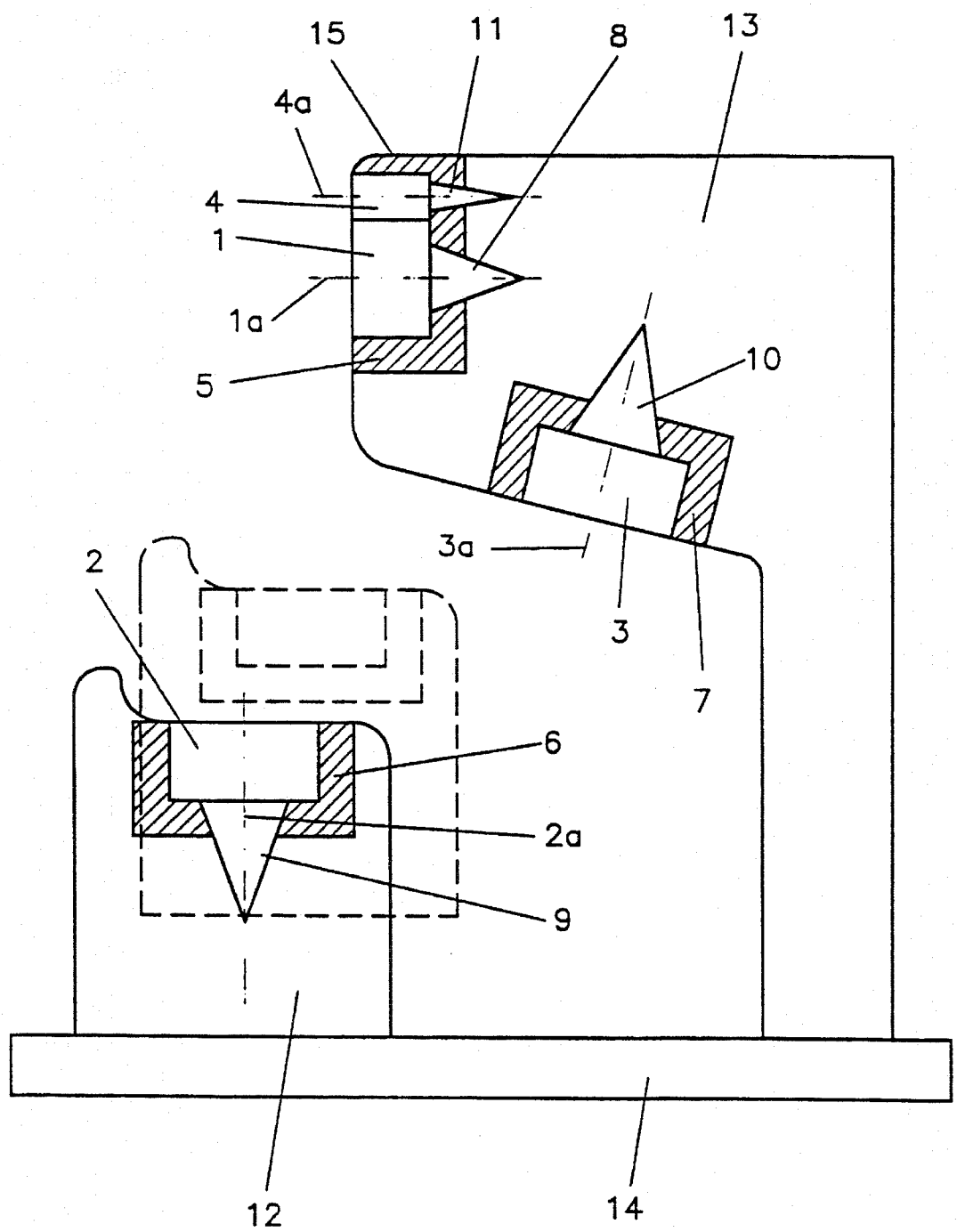

DETECTOR SYSTEM FOR DIRECT INTERNAL DOSIMETRY IN HUMAN BEINGS

The present application is a continuation-in-part application of International application PCT/EP93/01783 of Jul. 8, 1993 claiming the priority of German application P 42 22 661.9 of Jul. 10, 1992.

BACKGROUND OF THE INVENTION

The present invention relates to a detector system for direct internal dosimetry in a person, which system is capable of measuring the actual dose equivalent to which the person is exposed.

Basically such systems are known, for example, from IEEE Transactions on Nuclear Science, Vol. N5-J4, No. 1, 187, pages 606–610.

For radioactive substance ingestion monitoring for work-related radiation exposure of persons it is the object to determine the radioactivity exposure of the persons so that the limits set by the government are not exceeded. In addition it is necessary for the monitoring procedure to make sure that the supplemental doses resulting from active particle ingestion will not exceed the limits for body or organs as determined by law.

Body contamination monitoring can be performed by measuring the activity before entry into the body (monitoring of ambient air, that is, breathing air), by measuring the activity after entry into the body (direct monitoring) or by measuring the activity after exiting the body (excrement monitoring). Generally, direct monitoring supplies the most reliable evidence with regard to radioactivity ingestion and the resulting equivalent dosis. Direct monitoring however is usable only in connection with radionuclides which emit gamma or x-ray radiation of sufficient energy and intensity. However, this prerequisite is present in many areas of nuclear technology and of medicine so that, in these areas, direct monitoring is generally preferred.

The direct monitoring of body activity is performed with full or partial body counters which, with monitoring periods of between 5 and 20 minutes, measure the activity in the whole body or, respectively, in certain predetermined parts of the body. The persons to be monitored are checked after predetermined periods wherein the check-up frequency is dependent on the limits for the activity ingestion, the biological half-life and the lower detection limit of the whole or partial body monitors. Generally, the check-up frequencies are between 1 and 12 check-ups per year.

If, during such a routine check-up, a significant body activity is discovered, it will first be necessary to estimate the cause of the activity ingestion and, in a second step, to estimate the resultant equivalent dosis. For this, the following pieces of information are needed:

- ingestion time, that is, a time sample of the activity ingestion;
- path of ingestion and chemical composition of the ingested activity;
- individual metabolism;
- contribution of earlier ingestions to the actual measured value.

These pieces of information are generally not available or they are available only to an insufficient degree so that the estimate may be quite inaccurate. With nuclides with a relatively long biological half-life and with relatively simple and well-known metabolism behavior such as cesium-137, errors of between 25% and 100% are possible. With other nuclides the error may well be greater than a factor of 2.

Because of the multitude of the ingestion possibilities it is extremely difficult to define generally valid procedures for estimating the activity ingestion and the resulting equivalent dosis. The procedures given in the guidelines for the implementation of the radiation protection rules are necessarily a compromise between the clarity of the representation and the multiplicity of the required detail information. For this reason, numerous vague information details are entered in praxis during implementation of the guidelines. These vague factors result, among others, in the following difficulties:

It is practically impossible to provide general qualification features such as recognition limits, detection limits and reliability ranges for the activity ingestion and the resulting equivalent dosis. Consequently, it is very difficult to compare different monitoring procedures with one another. Furthermore, it is very difficult to define minimum requirements for the ingestion measurement locations.

It is very difficult to document the measurement values in such a manner that they can be repeated in a later test measurement. These difficulties are especially grave in the documentation of the measurement results in the radiation exposure cards of persons with changing workplace. The difficulties are present to an even greater degree if the results of the internal radiation exposure are to be documented in a central dosis recording location.

If a person with a given ingestion is tested at different institutions it has been found that often quite different activity ingestion, that is, different equivalent dosis, have been estimated. This can be highly confusing especially with a change of workplace.

It is the object of the present invention to provide a detector system for internal dosimetry with which the effective equivalency dosis of a person can be directly measured.

SUMMARY OF THE INVENTION

In a detector system for direct internal dosimetry of persons which comprises at least three gamma radiation detectors mounted on a support structure including a seat-like structure on which a person is supported in a seated position, the support structure has a first one of the detectors mounted thereon such that its central axis is directed toward the lungs of the person, a second detector mounted into the seat-like structure such that its central axis is directed upwardly toward the center of the digestive tract and a third detector arranged so that it is disposed above and its unshielded face is directed downwardly toward the legs of the person being checked for determining gamma ray emission from the whole body of said person.

With presently available whole body counters detectable nuclides are generally characterized in that their decay is accompanied by the emission of intense gamma radiation with an energy of more than 100 keV. If such a nuclide is present in a particular organ or body tissue there is a well-defined relation between the body internal activity and the photon flux at the body surface. The whole body dosimetry as presently practiced is based on this relationship.

However, there is a further given relationship between the photon flux at predetermined points of the body surface and the equivalency dosis effect. This relationship can be utilized, under certain conditions, in connection with internal radiation exposure for direct measurement of the equivalency dosis effect.

The procedure based on this relationship will be designated as direct internal dosimetry.

In accordance with the concept of dosimetry as defined by the internal radiation protection commission there is for the equivalency dosis effect in connection with internal radiation exposure the following relationship:

$$H^1(T,S) = 1.38 \times 10^4 \times A_S \times SEE(T,S) \quad (1)$$

wherein:
- $H^1(T,S)$ is the equivalency dosis effect in nSv/d generated in a particular target organ by nuclide deposition in a particular source organ S;
- $A_S$ is the activity of the nuclide deposition in the source organ S in Bq;
- $SEE(T,S)$ is the so-called specific effective energy of S on the basis of T (the energy per mass unit absorbed by the decay of the nuclide deposited in S, multiplied by a quality factor corresponding to the radiation quality of the respective nuclide in MeV/g/decay.

The SEE factors are given in tables for all important nuclides in "Limits for Intakes of Radionuclides by Workers", ICRP Publication 30, Part 1, Annals of the ICRP, Vol. 2, ¾, Pergamon Press, Oxford 1979.

The contribution of the target organ T to the actual equivalency dosis effect can be determined from equation (1) by multiplication with an organ-specific weighting factor $W_T$:

$$H_{eff}^1(T,S) = 1.38 \times 10^4 \times A_S \times W_T \times SEE(T,S) \quad (2)$$

With gamma radioactive nuclides, generally several target organs are affected such that the total actual equivalency dosis effect is the sum of the individual contributions of all target organs:

$$H_{eff}(S) = 1.38 \times 10^4 \times A_S \times \Sigma_T[W_T \times SEE(T,S)] \quad (3)$$
$$= A_S \times h(S)$$

wherein:

$$h_S = 1.38 \times 10^4 \times \Sigma_T[W_T \times SEE(T,S)] \quad (4)$$

The equivalency dosis effect factor h(S) defined in this manner permits the direct determination of the equivalency dosis effect from the activity in the source organ S.

If the internal body activity resides in several source organs, the total actual equivalency dosis effect is the sum of the contributions of all the source organs:

$$H_{eff}^1 = \Sigma_S[H_{eff}^1(S)] = \Sigma_S[A_S \times h(S)] \quad (5)$$

TABLE 1

| Depot S | Dosis effect factor h(S) (nSv/d per Bq Co-60) |
| --- | --- |
| Total Body | 0.20 |
| Lungs | 0.43 |
| Liver | 0.35 |
| Intestines | 0.72 |
| Upper Rectum | 0.80 |

TABLE 1-continued

| Depot S | Dosis effect factor h(S) (nSv/d per Bq Co-60) |
| --- | --- |
| Lower Rectum | 1.20 |

Table 1 gives some examplary values of h(S) for Co-60. In accordance therewith a time constant, that is, a time averaged-homogeneous total body activity of about 1 Bq Co-60 leads to an actual equivalency dosis effect of a level of 0.20 nSv/d. If the Co-60 activity resides in a dosis-relevant organ, the resulting actual equivalency dosis effect is correspondingly higher. For example, 1 Bq Co-60 in the lungs results in 0.43 nSv/d and the same amount in the lower rectum results in 1.2 nSv/d.

For direct measurement of the actual equivalency dosis effect a detector system is needed whose system sensitivity is suitably adapted to the factors h(S). From the values h(S) given in Table 1 it can be immediately recognized that such a system must include several detectors.

In the following considerations the number of detectors remains undetermined at first. The counting rate of the $i^{th}$ detector for nuclide deposition in the source organ S is determined as:

$$Zi(S) = e_i(S) \times A_S \quad (6)$$

wherein:
- $Zi(S)$ is the counting rate of the $i^{th}$ detector for nuclide depositions in the source organ S in imp/s;
- $e_i(S)$ is the sensitivity of the $i^{th}$ detector for nuclide depositions in the source organ in imp/s/Bq;
- $A_S$ is the activity in the source organ S in Bq.

The measurement value of the system is assigned the following linear combination of the counting rates of the various detectors:

$$M(S) = \Sigma_i[\alpha_i \times Zi(S)] = \Sigma_i[\alpha_i \times e_i(S)] \times A_S = m(S) \times A_S \quad (7)$$

wherein:
- $M(S)$ is the measurement value of the system for nuclide deposition in the source organ S in imp/s;
- $\alpha_i$ is the weighting factor for the $i^{th}$ detector with the normalization $\Sigma_i \times \alpha_i = 1$;
- $A_S$ is the activity in the source organ S in Bq;
- $m(S)$ is the system sensitivity for nuclide depositions in the source organ S in imp/s/Bq $$m(S) = \Sigma_i[\alpha_i \times e_i(S)]$$

If the internal body activity is generated by several source organs the measurement value is determined as follows:

$$M = \Sigma_S M(S) = \Sigma_S[m(S) \times A_S] \quad (8)$$

or $$M = \Sigma_i[\alpha_i \times \Sigma_S Zi(S)] = \Sigma_i[\alpha_i \times Zi] \quad (9)$$

wherein Zi is the total impulse rate of the $i^{th}$ detector.

If there is now with the nuclides to be detected for all possible source organs to be taken into consideration the relationship:

$$h(s) = K \times m(S) \tag{10}$$

wherein K is a constant calibration factor, the actual equivalency dosis effect can then be calculated directly from the measurement value M in accordance with the relationship:

$$H_{\text{eff}}^1 = \Sigma_S[h(S) \times A_S] = \Sigma_S[K \times m(S) \times A_S] = K \times M \tag{11}$$

Herein resides the principle of the direct measurement of the actual equivalency dosis effect of internal radiation exposure.

The invention will now be described in greater detail on the basis of a particular embodiment with reference to the FIGURE.

BRIEF DESCRIPTION OF THE DRAWING

The sole FIGURE shows schematically a detector arrangement according to the invention.

DESCRIPTION OF A PREFERRED EMBODIMENT

As shown in the FIGURE the detectors 1, 3 and 4 are supported in a housing 13 which also carries protective shields 5 and 7 and signal evaluation modules 8, 10 and 11. The evaluation modules consist of photomultipliers with high voltage supplies, preamplifiers and main amplifiers/discriminators. The housing is firmly mounted on a bottom plate 14 which also carries a housing 12 for a detector 2 with protective shield 6 and signal evaluation module 9.

The shields 5, 6 and 7 consist of 5 cm thick lead (which does not need to have a particularly low activity by itself).

The detector 1 is directed toward the lungs, the bronchi and the associated lymph nodes. The measuring arrangement is so optimized that, for people with body sizes of 150 to 200 cm, the mass center of the lungs is at most 2 cm from the central axis of the detector 1. The size and shielding of the detector have also been optimized so that, for people with body sizes of 150 to 200 cm, the detector window is fully covered and, with a person (reference person) of 170 cm height, the detector sensitivities for nuclide depositions in the area of the lungs, the upper abdomen area and the lower abdomen area are at a ratio of 12:6:1.

The detector 2 is directed toward the digestive system. The measuring arrangement has been optimized in such a manner that the body axis of the person is disposed normal on the detector window and is displaced from the center axis of the detector by not more than 2 cm. The size of the detector was optimized such that a) for persons with body sizes of 150 cm to 200 cm the detector window is fully covered and b) for a reference person (body size 170 cm) the detector sensitivities for nuclide depositions in the area of the lungs, the upper abdomen and the lower abdomen are at a ratio of 1:3:20.

The small housing 12 is movable relative to the large housing 13. It serves as a seat structure for a person to be checked. Moving distances for the seat structure are 15 cm horizontally and 15 cm vertically. Adjustment of the seat structure is done individually on the basis of the biometric parameters (body size, body weight, chest circumference) given on the identification card. The individual adjustment of the seat structure guarantees the optimization criteria given above.

The detector 3 is directed toward the thighs and the knees. The measuring arrangement has been optimized in such a manner that for persons with body sizes of 150 cm to 200 cm the mass center of the thighs is within 3 cm from an iso response curve (the curve interconnecting points of the same sensitivity) and the center point between the hollow of the knees is within 5 cm from a given reference point. This reference point is disposed on the center axis of the detector 20 cm in front of the detector window. In this manner for all persons almost the same sensitivity for homogeneous total body depositions is obtained. Furthermore the measuring arrangements are optimized in such a way that the radiation from the dosis relevant organs reaches the detectors under an angle of at least 120° and accordingly and, consequently, will not essentially contribute to the value measured by detector 3.

The detector 4 is integrated in the shield 5 in the embodiment shown. The top surface of the shield 5 may have a support surface 15 for supporting the chin of a person to be checked.

The detector 4 is only important for the incorporation of nuclides which are of particular importance with regard to the thyroid glands such as I-131 and Tc-99m. It is disposed at the height of the thyroid glands and has a size of 6×6×10 cm. For the detection of the remaining nuclides the system formed by the detectors 1 to 3 is sufficient.

The detectors 1 to 3 are partially shielded plastic scintillation detectors with crystal dimensions of 20 cm×20 cm×10 cm. The detectors are operated by simple electronics comprising a high voltage power supply, a preamplifier and a main amplifier/discriminator. The detector signals are fed into a PC via a data acquisition unit and are processed there for the determination of the actual equivalency dosis effect.

The person to be checked is seated on the seat structure with the detector 2 and initiates the measuring procedure with both hands by actuating two buttons (not shown) at the sides of the system. With the arrangement of the seat structure and of the operating buttons a relatively easily reproducible measuring position is insured in which especially the breathing tract and the digestive tract are disposed at predetermined distances from the respective detectors independently of the size of a particular person.

TABLE 2

| Depot S | Sensitivity $e_i(S)$ (Imp/s/Bq Co-60) | | |
|---|---|---|---|
| | Det. 1 | Det. 2 | Det. 3 |
| Total Body | 0,022 | 0,026 | 0,016 |
| Lungs | 0,114 | <0,001 | <0,001 |
| Liver | 0,058 | 0,014 | <0,001 |
| Small Intestine | 0,010 | 0,067 | <0,001 |
| Upper Rectum | 0,014 | 0,058 | <0,001 |
| Lower Rectum | <0,001 | 0,110 | 0,001 |

Table 2 shows, for example, the sensitivities of the detectors 1 to 3 determined for the measuring position for homogeneous Co-60 depositions in a whole body and in various dosis relevant organs. If these values are multiplied by the weighting factors.

$$\alpha_1 = 0,91$$
$$\alpha_2 = 2,72 \tag{12}$$
$$\alpha_3 = -0,263$$

the values of the system sensitivity in (S) are obtained according to equation (7) which values are given in Table 3.

TABLE 3

| Depot S | System Sensitivity m(S) (imp/s/Bq Co-60) |
|---|---|
| Total Body | 0,049 |
| Lungs | 0,104 |
| Liver | 0,091 |
| Small Intestine | 0,191 |
| Upper Rectum | 0,171 |
| Lower Rectum | 0,297 |

If these values are compared with the dosis effect factors h(S) given in Table 1 it becomes apparent that the relationship defined by equation (10) is reasonably correct for all depositions of Co-60. For the calibration factor K the following is obtained in accordance with equation (10):

$$K=4,1\pm 0,3 \text{ nSv/d pro imp/s} \quad (13)$$

Accordingly it is possible with the detector system proposed herein to directly determine the actual equivalency dosis effects for all distribution samples in principle with an error of less than 10%.

With other nuclides or nuclide mixtures a comparable accuracy can be achieved after corresponding adaptation of the weighting factors $\alpha$ and the calibration factor K. If the involved nuclides or nuclide compositions are not known it is necessary to operate with standard values and make allowances for greater errors. On the basis of presently available results it is appropriate to use as standard values the values given for Co-60 by way of equations (12) and (13). With these standard values the values given in Table 4 for the system sensitivity m(S) for homogeneous total body depositions of some selected nuclides are determined. These nuclides are the most important fission and activation products occurring during work in the nuclear field.

TABLE 4

| Nuclide | System Sensitivity m(S) (Imp/s/Bq) |
|---|---|
| Co-60 | 0,049 |
| Cs-137 | 0,025 |
| Zn-65 | 0,014 |
| Sb-124 | 0,048 |
| Co-58 | 0,037 |
| Ag-110 m | 0,088 |
| Mn-54 | 0,028 |
| Zr-95 | 0,057 |
| Ce-144 | 0,0026 |
| Ba-140 | 0,068 |
| Ru-106 | 0,010 |

TABLE 5

| | Relative Dosis Effect Indication for Homogeneous Depositions in | | | | | | |
|---|---|---|---|---|---|---|---|
| Nuclide | Lungs | SI | ULI | LLI | Liver | Other | - GK[a] |
| Co-60 | 0,99 | 1,09 | 0,88 | 1,01 | 1,07 | | 1,00 |
| Cs-137 | 0,44 | | | | | | 1,01 |
| Zn-65 | 1,42 | 1,18 | 1,11 | 1,39 | | 1,55[b] | 1,31 |
| Sb-124 | 0,50 | 0,84 | 0,55 | 0,64 | 1,04 | 0,93[b] | 0,93 |
| Co-58 | 2,00 | 1,78 | 1,42 | 1,83 | 2,16 | | 1,99 |
| Ag-110 m | 1,67 | 1,41 | 1,26 | 2,19 | 1,56 | 2,16[c] | 1,72 |
| Mn-54 | 2,02 | 1,59 | 1,42 | 1,92 | 1,63 | | 1,84 |
| Zr-95 | 1,23 | 1,51 | 1,07 | 1,30 | | 0,86[b] | 2,11 |
| Ce-144 | 0,01 | | 0,02 | 0,02 | 0,03 | 0,02[b] | 0,09 |
| Ba-140 | 0,36 | 0,70 | 0,42 | 0,48 | | 1,07[c] | 0,90 |

TABLE 5-continued

| | Relative Dosis Effect Indication for Homogeneous Depositions in | | | | | | |
|---|---|---|---|---|---|---|---|
| Nuclide | Lungs | SI | ULI | LLI | Liver | Other | - GK[a] |
| Ru-106 | 0,04 | 0,11 | 0,05 | 0,06 | | 0,03[c] | 0,14 |

[a]) total body;
[b]) bones;
[c]) stomach content

The system sensitivities given in Table 4 result in the values provided in Table 5 for the relative dosis effect indication of the detector system utilizing standard values. Consequently a homogeneous Cs-137 whole body deposit is, with standard setting, almost exactly evaluated whereas a Cs-137 lung deposit is undervalued by about a factor of 2. But this is radiologically unimportant since, with Cs-137 incorporations, lung deposits do not provide any substantial contributions to the total exposure. The nuclides Zn-65, Co-58, Ag-110, Mn-54 and Zr-95 are slightly or moderately overvalued, whereas Sb-124 and Ba-140 are slightly to moderately undervalued. The nuclides Ce-144 and Ru-106 are comparatively strongly undervalued. If both of these nuclides are substantial contributors to the total dosis it is not possible to use the standard values. Otherwise, it is possible to obtain quite good results with the standard values. If the relative dosis values determined for the given nuclides, with the exception of Ru-106 and Ce-144, are averaged, the following is obtained:

Total body deposit: RD=1,42±0,49

Lung deposit: RD=1,18±0,65

SI-deposit: RD=1,26±0,38

ULI-deposit: RD=1,01±0,38

LLI-deposit: RD=1,34±0,61

Liver deposit: RD=1,49±0,46

Bone deposit: RD=1,11±0,38

Accordingly, total body deposits are overvalued, on the average, by 42% wherein an average error of about 35% is to be taken into consideration. Lung deposits are overvalued, on the average, by 18%, but here, an average error of about 55% has to be taken into consideration. Determining the root-mean-square value of the relative errors for the various depositions it is found that the average error is about 38%. The average overvaluation potential is about 26%.

In summary, the following statements can be made:

1. With regard to the ingestion of Co-60 the actual equivalency dosis effect can be measured, utilizing standard values, generally with an error of less than 10%.

2. With regard to the ingestion of other fission or activation products with sufficiently intense gamma radiation components such as Cs-137, Zn-65, Sb-124, Co-58, Ag-110m, Mn-54, Zr-95 and Ba-140, the actual equivalency effect, utilizing the standard values, is overvalued on the average by about 26% wherein an average error of 40% has to be taken into consideration.

3. With the ingestion of fission and activation products with weak gamma radiation components such as Ru-106 and Ce-144 the weighting and calibration factors have to be adhered in accordance with the nuclide compositions. With good adjustment of the factors the actual equivalency dosis effect can be determined for these nuclides generally with an error of less than 20%.

The lower detection limit depends essentially on the accuracy of the zero-effect assumption for the various detectors. The zero-effect is dependent, on one hand, on the intensity and the main incidence angle of the radiation and, on the other hand, on the shielding effects of the person under consideration. The first component can be accurately determined by routing zero-effect measurements so that any such error can be reduced to the statistic counting error. For the second component the individual body proportions have to be taken into consideration.

In test measurements performed by the inventor it has been found that, with detectors arranged at chest level, for a person having a weight of about 70 kg and average body proportions the zero-effect is about 12000 imp/min. With a measurement period of 20 s as it is desirable for routing check-ups, this corresponds to a zero-effect counting rate of about 4000 imp, that is, an average statistical counting error of about 60 imp. But as a result of the different effective shielding of the persons being checked the individual error width of the zero-effect counting rate is substantially greater than 60 imp per 20 s. However, the measurements show that the effective shielding can quite well be correlated to the chest circumference of the person being checked. For example, for persons with a chest circumference of between 80 and 120 cm, the zero-effect counting rate of the detectors can be estimated by way of an empiric formula with an average error of about 80 imp per 20 s. This value is only slightly above the statistic counting error to be expected over such a measuring period. Also the weight of the person to be checked can be utilized as control parameter wherein for the detector arranged at chest level as well as for the detector arranged below the seating surface an average error at a level of about 120 imp per 20 s is to be expected. For the detector arranged above the thighs the shielding effect provided by the body is relatively small so that no individual corrections are necessary. For this detector an average error at a level of about 80 imp per 20 s is to be expected. The error ranges mentioned above are for a setup of the detector system in a room in which no special shielding structures are installed. Accordingly, the given error ranges are the upper limits of the values actually achievable in practice.

For further considerations it is assumed for conservative reasons that the average error in the zero-effect prediction for all detectors is about 120 imp per s. Consequently the average error of the net counting rate for each detector is about 140 imp per s.

With equations (9, 11) the actual equivalency dosis effect is:

$$H_{eff}^1 = K \times M = K \times \Sigma_i [\alpha_i \times Zi] \quad (14)$$

wherein Zi is the impulse rate of the $i^{th}$ detector as caused by the ingestion. From equation (14) the average error of the actual equivalency dosis effect is determined as:

$$S^2(H_{eff}^1) = S^2(K) \times (\Sigma_i [\alpha_i Zi])^2 + K \times \Sigma_i [(\alpha_i)^2 \times S^2(Zi)] \quad (15)$$

wherein:
$S^2(H_{eff}^1)$ is the mean squared measure of deviation of $H_{eff}^1$;
$S^2(K)$ is the average mean measure of deviation of K;
$S^2(Zi)$ is the average mean measure of deviation of Z.

With standard values for the detector system, equation (13) provides for Co-60 ingestion:

K=4.1±0.3 nSv/d per imp/s

For other nuclides with a sufficiently high gamma radiation component on the basis of the above considerations, the following value can be assumed for K:

K=3.3±1.3 nSv/d per imp/s

The lower detection limit is suitably defined herein by the postulation that the mean error of the actual equivalency dosis effect must not be larger than 50%. With this requirement lower limits are determined on the basis of S(Zi)=140 imp per 20 s corresponding to S(Zi)=7 imp/s as follows:

$H_{eff}^1\emptyset$=0.17 µSv/d corresponding to 62 µSv/a with ingestion of Co-60 or limits of $H_{eff}^1\emptyset$=0.27 µSv/d corresponding to 99 µSv/a of unknown mixtures of nuclides with a sufficiently high gamma radiation component have been ingested.

These detection limits relate to one-time routine check-ups of 20 s duration. For regular weekly routine check-ups one can assume that the detector limit based on a year is surely smaller than the given values. Consequently it can be stated, in summary, that, for the ingestion of nuclides with a sufficiently high gamma radiation component, the lower detection limit of the procedure is less than 0.1 mSv/a. Consequently, it is comparable to the lower detection limit of external dosimetry procedures.

What is claimed is:

1. A detector system for direct internal dosimetry of a person, said system comprising a support structure with a bottom plate and with at least three lead-shielded detectors each having an unshielded face area with a central axis for detecting gamma radiation entering said detectors through said face area along said central axis, said support structure including a seat portion mounted on said bottom plate for supporting said person thereon in a seated position, a first one of said detectors being supported by said support structure such that its central axis is directed toward the mass center of the lungs of such person, a second detector mounted into said seat portion such that its unshielded face area is facing upwardly toward the center of the digestive tract of such person seated on said seat portion, and a third detector supported on said support structure such that its central axis is directed toward the legs of such person seated on said seat portion.

2. A detector system according to claim 1, wherein said unshielded face area of said first detector is disposed opposite the chest of said person when seated on said seat portion in an upright position, the central axis of said first detector being arranged essentially parallel to said bottom plate.

3. A detector system according to claim 1, wherein the unshielded face of said third detector is disposed opposite the thighs of said person sitting on said seat portion in an upright position in such a way that the angle between the center axis of the third detector and a line extending normal to said bottom plate is between 0° and 30°.

4. A detector system according to claim 1, further comprising another detector having a center axis, said detector being mounted on said support structure in such a manner that its center axis is directed toward the thyroid gland of the person seated on said seat portion.

5. A detector system according to claim 1, wherein said seat portion is supported on said base so as to be vertically and horizontally movable thereon.

* * * * *